United States Patent [19]
Baroody et al.

[11] Patent Number: 6,117,843
[45] Date of Patent: *Sep. 12, 2000

[54] COMPOSITIONS FOR THE TREATMENT OF ACNE CONTAINING CLINDAMYCIN AND BENZOYL PEROXIDE

[75] Inventors: Lloyd J. Baroody, 1940 Inverness Dr., Scotch Plains, N.J. 07076; Gordon J. Dow, 4189 Chaparral Ct., Santa Rosa, Calif. 95409; Debra A. Dow, Petaluma; Robert Lathrop, Novato, both of Calif.

[73] Assignees: Lloyd J. Baroody, Scotch Plains, N.J.; Gordon J. Dow, Santa Rosa, Calif.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/855,151

[22] Filed: May 13, 1997

Related U.S. Application Data

[63] Continuation of application No. 08/488,301, Jun. 7, 1995, abandoned, which is a continuation-in-part of application No. 08/235,125, Apr. 28, 1994, Pat. No. 5,733,886, which is a continuation of application No. 07/837,836, Feb. 18, 1992, abandoned.

[51] Int. Cl.$^7$ .................................................. A61K 31/70
[52] U.S. Cl. ............................. 514/24; 514/714; 514/859
[58] Field of Search ............................... 514/29, 714, 859

[56] References Cited

U.S. PATENT DOCUMENTS

| | | | |
|---|---|---|---|
| 5,446,028 | 8/1995 | Klen et al. | 514/43 |
| 5,466,446 | 11/1995 | Shefel et al. | 924/78.37 |

*Primary Examiner*—Elli Peselev
*Attorney, Agent, or Firm*—Chernoff, Vilhauer, McClung & Stenzel, LLP; Howard Eisenberg

[57] ABSTRACT

A pharmaceutical composition containing clindamycin and benzoyl peroxide is disclosed for the treatment of acne. The composition is stable for several months when stored at room temperature. Methods of preparing and of using the composition are disclosed.

15 Claims, 2 Drawing Sheets

COMPOSITIONS FOR THE TREATMENT OF ACNE CONTAINING CLINDAMYCIN AND BENZOYL PEROXIDE

This application is a continuation of application Ser. No. 08/488,301 filed Jun. 7, 1995, now abandoned, which is a continuation-in-part of application Ser. No. 08/235,125, filed Apr. 28, 1994, no U.S. Pat. No. 5,733,886, which is a continuation of application Ser. No. 07/837,836, filed Feb.18, 1992, now abandoned.

BACKGROUND OF THE INVENTION

1. Field of the Invention

The present invention relates generally to compositions and methods for formulating compositions for treatment of acne. More particularly, the present invention relates to compositions comprising benzoyl peroxide and clindamycin for treatment of acne by topical administration.

Acne is a common skin disorder characterized by blackheads, whiteheads, papules, pustules, cysts, and various sized nodules and scars which, in the inflammatory state of the disorder, are contaminated with bacteria such as *Propionibacterium acnes*. The disorder effects skin areas where the sebaceous glands are most active, and bacterial infection can occur in the sebaceous follicles.

A variety of acne treatment methods have been developed, D including both systemic and topical administration of antibiotics, topical administration of organic peroxides, particularly benzoyl peroxide, and the like. Of particular interest to the present invention is the topical administration of antibiotic compositions and other active ingredients, such as benzoyl peroxide.

A particularly effective topical composition for the treatment of acne is a combination of erythromycin, a topical antibiotic, and benzoyl peroxide, as described in U.S. Pat. No. 4,497,794. Compositions prepared generally as described in the '794 patent are sold under the tradename Benzamycin® by Dermik Laboratories, Inc., Collegeville, Pa. Benzamycin® is widely prescribed for the treatment of acne and is recognized in some cases to be more effective than treatment with either erythromycin or benzoyl peroxide alone.

The use of products which combine erythromycin and benzoyl peroxide, however, suffers from certain disadvantages. The combination of erythromycin and benzoyl peroxide is unstable and requires refrigeration for storage. The need to refrigerate the product is not only inconvenient for the patient (e.g., it is difficult to continuously refrigerate the product when travelling), the application of a cold medicine to the face is often unpleasant and reduces patient compliance. The need to store the product in a refrigerator can further reduce patient compliance since the product is "hidden away."

The Benzamycin® product suffers from particular formulation problems. In order to prepare the product, a pharmacist must dissolve erythromycin powder in alcohol from the pharmacy stock. Variations in particular alcohols which are available can lead to variability in the compounded product. Moreover, improper compounding by the pharmacist is possible because of the variable dissolution of erythromycin in alcohol resulting in partially dissolved or undissolved aggregates of the drug. As a result, the effective dosage of the compounded product can vary, and some patients have reported that the product sometimes feels "gritty" when applied to the skin.

For these reasons, it would be desirable to provide improved compositions and methods for formulating compositions for the treatment of acne. In particular, it would be desirable to provide products which combine the activity of an antibiotic compound with the activity of benzoyl peroxide, with none or fewer of the disadvantages described above for the combination of erythromycin and benzoyl peroxide. Such compositions should be effective in treating acne, preferably being at least as effective as the use of erythromycin/benzoyl peroxide compositions and more preferably being more effective than erythromycin/benzoyl peroxide compositions. The compositions should also overcome the formulation and stability problems which have been associated with the erythromycin/benzoyl peroxide compositions. That is, the improved compositions should be easy to formulate, should have a smooth consistency after formulation, should be adequately stable, and should have a sufficiently long storage life even without refrigeration.

2. Description of the Background Art

U.S. Pat. No. 4,497,794, discloses compositions combining erythromycin and benzoyl peroxide for the treatment of acne, as described above. Other patents disclosing the combination of erythromycin and benzoyl peroxide for acne treatment and other purposes include U.S. Pat. No. 4,411,893; U.S. Pat. No. 4,692,329; and British Patent No. 1,594,314. The combination of erythromycin with other organic peroxides for the treatment of acne is described in British Patent No. 2,088,717. Other formulations containing benzoyl peroxide for the treatment of acne are described in U.S. Pat. Nos. 3,535,422, 4,056,611; 4,318,907; 4,923,900; 4,387,107; and 4,228,163. Other peroxide formulations for treating acne are described in U.S. Pat. No. 4,607,101. The use of clindamycin and other lincomycin antibiotics for the treatment of acne is described in U.S. Pat. No. 3,969,516. Hirschmann (1988) Arch. Dermatol. 124:1691–1700 and Fulton, Jr., et al. (1974) Arch. Dermatol. 110:83–86 describe the topical use of antibiotics for the treatment of acne.

SUMMARY OF THE INVENTION

The present invention provides novel acne treatment compositions comprising both clindamycin, an antibiotic effective against *Propionibacterium acnes*, and benzoyl peroxide, a keratolytic and desquamative agent which further possesses a broad antibacterial activity. The two agents are combined in a Pharmaceutically acceptable fluid carrier, usually a gel, which has been found to provide effective topical treatment of acne. The benzoyl peroxide will be present in the carrier at a concentration from 1% by weight to 20% by weight and the clindamycin will be present at a concentration from 0.2% by weight to 4% by weight. By maintaining the compositions at a pH below 7, the tendency of benzoyl peroxide to oxidize and degrade clindamycin is largely overcome and the product remains stable during storage at room temperature for extended periods, typically several months or longer. Additionally, the compositions of the present invention have been found to remain substantially odor free even after storage at room temperature for extended periods. This is surprising since clindamycin solutions frequently develop a strong offensive odor upon aging. The presence of such an odor is unacceptable in topical formulations which are to be applied to a patient's face.

In a particular aspect of the present invention, the topical compositions are prepared by combining or admixing an aqueous gel suspension of benzoyl peroxide with an aqueous solution of a clindamycin salt or ester. Prior to combination, the two components are maintained individually, each at a pH selected to enhance stability of the component by itself. The individual pH of each component is further selected so that after combination, the pH of the final admixed product will produce a pH below 7 to provide stability at room temperature during a normal period of use, as described above. More specifically, the pH of the aqueous clindamycin solution is adjusted to a pH in the range from 3.5 to 7, where it is stable and can remain in solution for extended periods. The aqueous suspension of benzoyl peroxide is stored at a pH from 3.5 to 7.0, typically with a gelling agent which has a relatively low viscosity at the storage pH. By combining preselected amounts of the two components, the pH of the combination will be below 7 and the combination will remain stable for several months after admixture at room temperature.

Preparation of the topical compositions by combining two separately maintained components has a number of advantages. While the topical composition itself is stable for a period of months at room temperature, the individual components will be stable for much longer periods, typically for at least two years or longer. Thus, the components may be prepackaged and will have an acceptable shelf life after distribution. The individual components of the present invention are easily formulated prior to use. The benzoyl peroxide is present as a stable suspension and the clindamycin is present as a stable solution, and their combination requires simple mixing without the need to dissolve any dry components. Moreover, there is no need to combine any other ingredients, such as alcohol, from the pharmacist's stock solutions, thus lessening product variability. Additionally, by properly selecting the gelling agent, the initial viscosity of the benzoyl peroxide suspension (at the suspension pH) may be relatively low, while the viscosity of the final product (at the product pH), can be relatively high to provide a desired gel consistency. Thus, the components may be easily combined by a pharmacist to provide a gel having a pleasing consistency and texture for use by the patient.

The present invention further provides a kit for preparation of the topical composition from the individual components. The kit will comprise a first container holding the benzoyl peroxide suspension and a second container holding the aqueous solution of clindamycin salt or ester. In addition, the kit will include instructions to combine the benzoyl peroxide suspension with the clindamycin solution to provide the topical composition. Optionally, the kit may include a disposable mixing spatula for the convenience of the dispensing pharmacist.

The present invention still further comprises methods for treating acne by applying the topical composition to affected areas of the patient's skin.

DESCRIPTION OF THE PREFERRED EMBODIMENT

According to the present invention, topical compositions for the treatment of acne include both clindamycin and benzoyl peroxide present in a fluid carrier or vehicle which is formulated to enhance stability, efficacy, and aesthetic acceptability of the compositions. Preferably, the topical composition contains no active ingredients other than clindamycin and benzoyl peroxide. The clindamycin constituent will be a pharmaceutical grade salt or ester, usually being clindamycin phosphate. Clindamycin phosphate (ester) is preferred over clindamycin hydrochloride (salt) because of its wider compatibility with gelling agents and its more extensive history of topical use. The preparation of suitable clindamycin and equivalent lincomycin compounds are described in U.S. Pat. No. 3,969,516, the disclosure of which is incorporated herein by reference. Pharmaceutical grade clindamycin phosphate is available from commercial suppliers such as Genzyme Corporation, One Kendall Square, Cambridge Mass. 02139.

The benzoyl peroxide constituent will be pharmaceutical grade. It may be in the form of a slurry of a finely divided powder, typically having a mean particle size of 35 μm, or lower, or in the form of a hydrous granular material which will have its particle size reduced accordingly during processing according to this invention. Preparation of suitable benzoyl peroxide constituents is well described in the medical and patent literature. See, for example, the U.S. Pat. Nos. 3,535,422; 4,056,611; 4,387,107; and 4,923,900, the disclosures of which are incorporated herein by reference. Suitable benzoyl peroxide raw materials are available from commercial suppliers, such as the Norac Company, Azusa, Calif.

The clindamycin and benzoyl peroxide constituents will be combined in a suitable fluid vehicle or carrier, typically an aqueous carrier, and will preferably be further combined with an aqueous gelling agent, such as neutral, anionic, and cationic polymers, and mixtures thereof. Exemplary polymers include carboxy vinyl polymers, preferably carboxypolymethylene (CAS Registry No. 9007-209) which is commercially available under the tradename Carbopol®, from B.F. Goodrich Chemical Company, Cleveland, Ohio 44138. The most preferred gelling agent is Carbopol®. Other suitable gelling agents include cellulosic polymers, such as gum arabic, gum tragacanth, locust bean gum, guar gum, xanthan gum, cellulose gum, methylcellulose, hydroxyethylcellulose, hydroxypropylcellulose, and hydroxypropylmethylcellulose.

As discussed in more detail below, the gelling agent will usually be initially combined with an aqueous suspension of benzoyl peroxide to form a first component of a two component kit for formulating the topical composition. The gelling agent ideally will be selected to have a reduced viscosity at the pH of the first component and an increased viscosity at the stage of the final product obtained when the two components are combined.

Other ingredients which may optionally be provided in the topical compositions include humectants, such as propylene glycol; solvents, such as alcohol; and anti-microbial preservatives, such as methylparaben and propylparaben. The topical compositions will also include an organic or inorganic base, such as potassium hydroxide, which is used to adjust the pH of the initial components and the final product, as described in more detail hereinbelow.

Preferably, the topical compositions do not include nicotinic acid or nicotinamide.

Table 1 sets forth exemplary formulations for the topical compositions of the present invention and Table 2 sets forth a preferred formulation.

TABLE 1

| Constituent | Weight Percent[1] | |
|---|---|---|
| | Broad Range | Preferred Range |
| Clindamycin | 0.2% to 4% | 1% to 2% |
| Benzoyl peroxide | 1% to 20% | 2.5% to 10% |
| Gelling agent | 0.1% to 5% | 0.5% to 2% |
| Huinectant | 0% to 30% | 5% to 15% |
| Antimicrobial preservative | 0% to 2% | 0.1% to 0.5% |
| Solvent | 0% to 50% | 0% to 20% |
| Buffer, acid or base | pH 4 to <pH 7 | pH 4.5 to pH 5.5 |

[1]Based on total weight in purified water or other suitable fluid carrier.

TABLE 2

| Constituent | Weight Percent[1] |
|---|---|
| Clindamycin | 1.0 |
| Benzoyl peroxide | 5.0 |
| Carboxyl vinyl polymer | 1.25 |
| Propylene glycol | 10.0 |
| Methylparaben | 0.2 |
| Propylparaben | 0.05 |
| pH | 5.0 |

[1]Based on total weight in purified water.

The two-component kit will comprise an aqueous solution of clindamycin having a concentration in the range from 2% to 15% by weight, preferably being in the range from 8% to 12% by weight. It is important that the pH of the solution be maintained within a range from 3.5 to 7, preferably within a range from 6 to 6.5, in order to inhibit precipitation of the clindamycin from the solution, particularly when the solution is exposed to cold temperatures during storage. The pH of an aqueous clindamycin phosphate solution is normally about 3.5, and the pH of the clindamycin component may be increased to within the desired range by the addition of a pharmaceutically acceptable buffer or base, such as potassium hydroxide.

The benzoyl peroxide component of the two-component kit will comprise an aqueous suspension (stable dispersion) of benzoyl peroxide and a concentration in the range from 1% to 20% by weight, preferably in the range from 5% to 10% by weight. The benzoyl peroxide component will also contain the gelling agent, when a gelling agent is present in the combined topical composition. By properly selecting the nature of the gelling agent and the pH of the benzoyl peroxide component, the benzoyl peroxide component itself may be maintained at a relatively low viscosity while the final topical composition (which is at a different pH) will have a relatively higher viscosity. In this way, mixing of the two components to form the topical composition is facilitated (i.e. the lower viscosity of the benzoyl peroxide component makes the combination and mixing with the clindamycin component easier) while the final topical composition can still possess the desired higher viscosity, gel consistency.

Preferably, the viscosity of the benzoyl peroxide i component will be below about $9 \times 10^4$ cp, usually being in the range from $5 \times 10^4$ cp to $9 \times 10^4$ cp, more preferably being in the range from $6.5 \times 10^4$ cp to $8.5 \times 10^4$ cp, while the viscosity of the final topical composition product will be in the range from $7 \times 10^4$ cp to $12 \times 10^4$ cp, more preferably being in the range from $8 \times 10^4$ cp to $10 \times 10^4$ cp. These viscosities may be achieved using the polymeric gelling agents, as described above, and a benzoyl peroxide component having a pH in the range from 3.5 to 7.0, preferably in the range from 4.0 to 5.0. The pH may be adjusted by the addition of a pharmaceutically acceptable buffer or base, such as potassium hydroxide. When the benzoyl peroxide component is combined with the clindamycin component, the resulting combined product will have an increased pH resulting in enhanced viscosity within the range set forth above.

The variation of viscosity with pH in a preferred Carbopol® gelling agent is as set forth in Table 3:

TABLE 3

| Effect of pH on Viscosity of 0.5 Weight % Solutions of Carbopol ® 940 | |
|---|---|
| pH | CP |
| 4.0 | 23,500 |
| 4.5 | 38,500 |
| 5.0 | 48,500 |
| 6.0 | 56,800 |
| 6.5 | 57,800 |
| 7.0 | 57,900 |

Thus, it can be seen that a beneficial increase in viscosity can be achieved by increasing the pH of the final (combined) product relative to the initial pH of the benzoyl peroxide component containing the gelling agent.

The additional constituents, such as the anti-microbial agents, solvents, humectants, and the like, may be present in either the clindamycin component, the benzoyl peroxide component, or both. Such constituents will be present in the individual kit components at concentrations which result in the desired final concentrations in the topical composition, such as set forth in Table 1 above.

The clindamycin component and the benzoyl peroxide component will be stored in separate, sealed containers, such as bottles, jars, vials, ampules, tubes, pouches, and the like, with the two containers usually being packaged together in the form of a kit, usually including instructions on how to admix the final product, and optionally including a mixing spatula. In this way, the kits may be manufactured, distributed, and stored at remote locations where they will be used, typically by pharmacies, hospitals, doctor's offices, and the like. The kits will have an extended shelf life, typically being at least a year, usually being at least two years, or longer so long as the clindamycin component and benzoyl peroxide component are formulated as described above.

Figure 1:
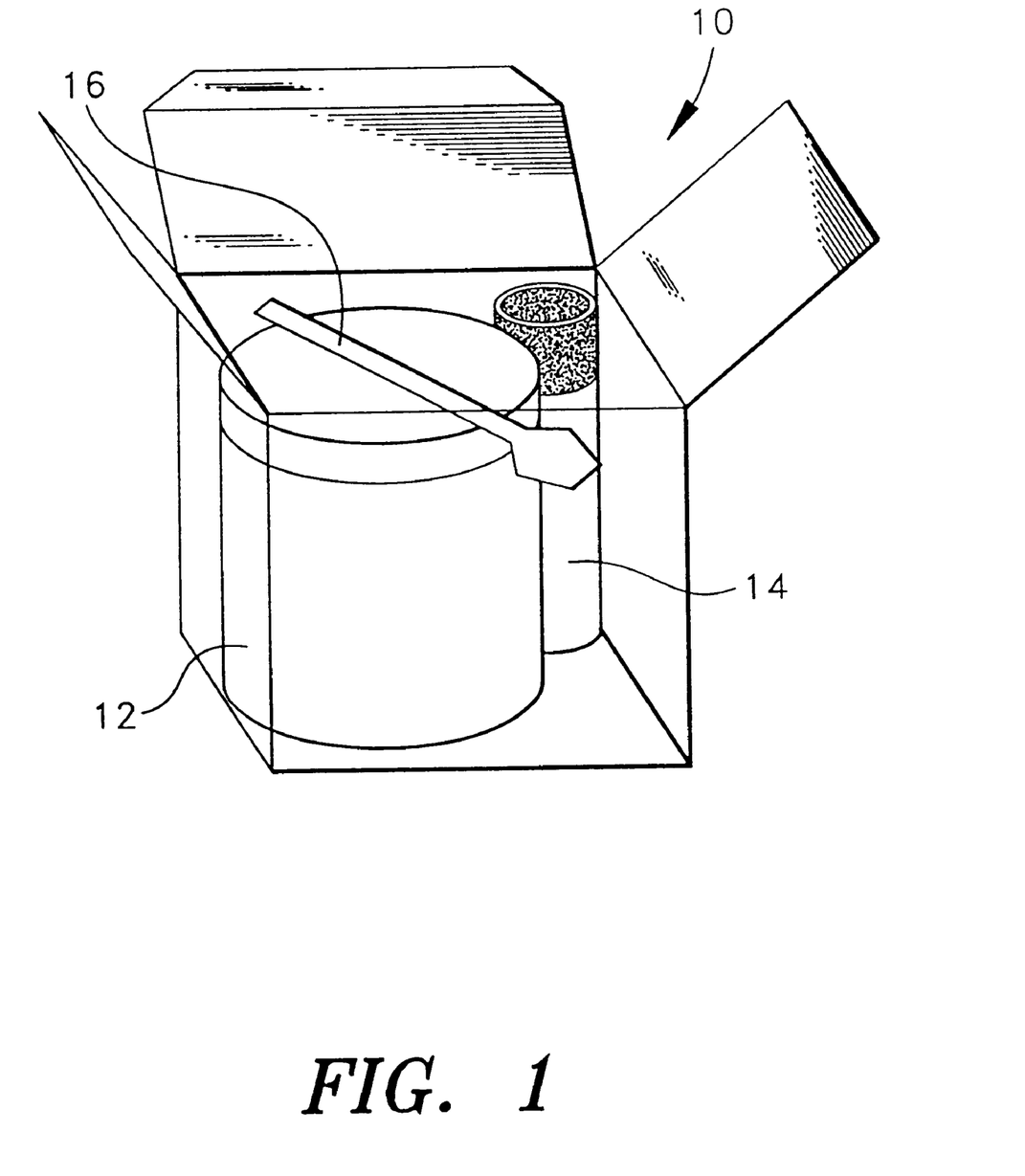
FIG. 1 illustrates a kit according to the present invention.

Conveniently, when packaged together as a kit 10 (FIG. 1), the benzoyl peroxide component will be stored as a low viscosity gel in a jar or other container suitable for mixing. The kit instructions (not illustrated) will call for combining the contents of the clindamycin component container, typically a vial 14, into the benzoyl peroxide container 12 and for subsequently mixing the combination to a uniform consistency. Optionally, the kit 10 may include a disposable spatula 16 for mixing so that the user or pharmacist need not employ any outside materials to formulate the final topical composition.

The relative amounts of the benzoyl peroxide composition and the clindamycin composition in each of the containers will be selected to provide the desired final volume of the topical composition as well as providing the desired final concentrations of the active constituents. Preferably, the ratio of clindamycin solution component to benzoyl peroxide suspension component is in the range of 1 or 2 to 9. Larger proportions of the clindamycin solution can be used, for example, a 1 to 1 ratio of the components, however such a ratio is less preferred because of the increased mixing time required to achieve homogeneity of the admixture. For example, the mixing time for a 1 to 1 ratio of components is twice as long or longer than that for the preferred ratio of about 1 or 2 to 9. The ability to maintain the preferred ratio is at least partly the result of stable incorporation of relatively high concentrations of clindamycin in the clindamycin component at the preferred pH range from 6 to 6.5.

Usually, the total weight of topical composition prepared from a single kit will be in the range from 5 g to 120 g, usually being in the range from 15 g to 45 g. When the clindamycin component is to be added to the benzoyl peroxide component, the weight of the benzoyl peroxide will typically be greater, usually being in the range from 2.5 g to 100 g, more usually being in the range from 12 g to 40 g. The weight of the clindamycin component will usually be in the range from 0.5 g to 60 g, more usually being in the range from 1.5 g to 7 g. The precise weights, volumes, constituent concentrations, pH levels, and the like, are of course all interdependent and must be finally selected to provide the desired characteristics set forth above for the final and mixed product. The determination of the precise formulations for the individual constituents is well within the skill of the art.

The fully formulated (admixed) topical compositions of the present invention may be stored at room temperature and will remain stable, i.e., without substantial loss of efficacy or unacceptable loss of the clindamycin content, for extended periods, typically for at least one month, frequently for two months or longer, and usually for three months or longer.

The topical compositions of the present invention are used to treat acne by applying a thin layer of the composition to the affected area of the skin. Usually, from 0.1 g to 1 g of the topical composition will be applied in a single application, with applications being repeated at least daily, usually being repeated twice daily, and sometimes being repeated at frequency of three times daily or greater.

The following examples are offered by way of illustration, not by way of limitation.

EXPERIMENTAL

Examples 1–4

Aqueous solutions of clindamycin (Genzyme Corp.) were prepared as follows:

|  | Weight Percent | | | |
| --- | --- | --- | --- | --- |
| Component | Ex. 1 | Ex. 2 | Ex. 3 | Ex. 4 |
| Clindamycin Phosphate Ester | 10.58 | 2.38 | 14.28 | 0 |
| Clindamycin Hydrochloride Salt | 0 | 0 | 0 | 7.50 |
| Methylparaben | 0.10 | 0.10 | 0 | 0.10 |
| Propylparaben | 0.02 | 0.02 | 0 | 0.02 |
| Imidurea | 0 | 0 | 0.3 | 0 |
| Potassium Hydroxide, 10% Aqueous Solution (QS) | pH 6.2 | pH 4.5 | pH 6.5 | pH 6.9 |
| Purified Water (QS ad) | 100.00 | 100.00 | 100.00 | 100.00 |

The methylparaben and propylparaben or imidurea were first dissolved in water equivalent to about 75% of the total batch amount. Next, the clindamycin component was added and mixed. After the clindamycin had mostly dissolved, the potassium hydroxide solution was added incrementally (while mixing) to reach the desired pH. Finally, water was added to make the formulation total 100%.

Examples 5–8

Benzoyl peroxide aqueous suspensions were prepared as follows:

|  | Weight Percent | | | |
| --- | --- | --- | --- | --- |
| Component | Ex. 5 | Ex. 6 | Ex. 7 | Ex. 8 |
| Hydrous Benzoyl Peroxide, USP (70%) | 8.67 | 17.34 | 5.00 | 8.67 |
| Imidurea | 0 | 0 | 0.3 | 0 |
| Methylparaben | 0.23 | 0.18 | 0 | 0.20 |
| Propylparaben | 0.06 | 0.06 | 0 | 0.05 |
| Propylene glycol | 11.56 | 7.50 | 0 | 15.00 |
| Carboxy vinyl polymer | 1.45 | 2.0 | 1.0 | 1.45 |
| Potassium Hydroxide, 10% Aqueous Solution (QS) | pH 4.5 | pH 4.3 | pH 4.7 | 0 |
| Trolamine, NF (QS) | 0 | 0 | 0 | 6.5 |
| Purified Water (QS ad) | 100.00 | 100.00 | 100.00 | 100.00 |

The imidurea, methylparaben, propylparaben and/or propylene glycol were first dissolved in an amount of water equivalent to about 65 percent of the total batch amount. The carboxy vinyl polymer was then added slowly while the dispersion was vigorously mixed. While mixing, the potassium hydroxide solution or trolamine was added incrementally to the carboxyl vinyl polymer dispersion to achieve the desired pH. The benzoyl peroxide was levigated with a portion of the carboxy vinyl polymer dispersion and passed through a homogenizer or mill several times until the average particle size was less than 25 microns in diameter. Finally, the benzoyl peroxide dispersion and the remainder of the water were added and mixed into the suspension until homogeneous.

Example 9

Another aqueous suspension of benzoyl peroxide was prepared from pre-micronized benzoyl peroxide as follows:

| Component | Weight Percent |
| --- | --- |
| Hydrous Benzoyl Peroxide, 40%, micronized | 15.17 |
| Propylene Glycol | 11.5 |
| Methylparaben | 0.20 |
| Propylparaben | 0.05 |
| Carboxy Vinyl Polymer | 1.45 |
| Potassium Hydroxide, 10% Aqueous Solution (QS) | pH 4.5 |
| Purified Water (QS ad) | 100.00 |

The methylparaben, propylparaben and propylene glycol were dissolved in an amount of water equivalent to about 60 percent of the total batch amount. The carboxy vinyl polymer was then added slowly while the dispersion was vigorously mixed. While mixing, the potassium hydroxide solution was added incrementally to the carboxy vinyl polymer dispersion to achieve the desired pH. The benzoyl peroxide was mixed vigorously with the remaining portion of the water. Finally, the benzoyl peroxide slurry was added to the carboxy vinyl polymer dispersion and mixed until homogeneous.

Example 10

A kit was prepared which included (a) 4 g of the clindamycin aqueous solution of Example 1 in a 4 mL amber glass screw cap vial, (b) 26 g of the benzoyl peroxide aqueous suspension from Example 5 in a 1 ounce wide mouth plastic jar, and (c) a disposable mixing spatula.

The components of the kit were admixed as follows:
1. The entire contents of the vial of clindamycin solution was added to the jar containing the benzoyl peroxide suspension; and
2. Using the disposable plastic spatula, the combination was mixed until the gel became homogeneous (about 1 minute).

An aesthetically pleasing white gel was produced containing about 5.26% benzoyl peroxide and about 1.2% clindamycin (1.4% measured as phosphate).

Example 11

A kit was prepared which included (a) 12 g of the clindamycin aqueous solution of Example 1 in a 15 mL amber glass screw cap vial, (b) 78 g of the benzoyl peroxide aqueous suspension from Example 6 in a 4 ounce wide mouth plastic jar, and (c) a disposable mixing spatula.

The components were admixed as follows:
1. The entire contents of the vial of clindamycin solution was added to the jar containing the benzoyl peroxide suspension; and
2. Using the disposable plastic spatula, the combination was mixed until the gel became homogeneous (about 1 minute).

An aesthetically pleasing white gel was produced containing about 10.5% benzoyl peroxide and about 1.2% clindamycin (1.4% measured as phosphate).

Example 12

A kit was prepared which included (a) 7.5 g of the clindamycin aqueous solution of Example 2 in an 8 mL amber glass screw cap vial, (b) 7.5 g of the benzoyl peroxide aqueous suspension from Example 6 in a one-half ounce wide mouth plastic jar, and (c) a disposable mixing spatula.

The components were admixed as follows:
1. The entire contents of the vial of clindamycin solution was added to the jar containing the benzoyl peroxide suspension; and
2. Using the disposable plastic spatula, the combination was mixed until the gel became homogeneous (about 1 minute).

An aesthetically pleasing white gel was produced containing about 6.07% benzoyl peroxide and about 1.0% clindamycin (1.18% measured as phosphate).

Example 13

A kit was prepared which included (a) 8 g of the clindamycin aqueous solution of Example 1 in an 8 mL amber glass screw cap vial, (b) 22 g of the benzoyl peroxide aqueous suspension from Example 7 in a one ounce wide mouth plastic jar, and (c) a disposable mixing spatula.

The components were admixed as follows:
1. The entire contents of the vial of clindamycin solution was added to the jar containing the benzoyl peroxide suspension; and
2. Using the disposable plastic spatula, the combination was mixed until the gel became homogeneous (about 1 minute).

An aesthetically pleasing white gel was produced containing about 2.56% benzoyl peroxide and about 2.3% clindamycin (2.8% measured as phosphate).

Example 14

Aqueous solutions of clindamycin phosphate were tested for chemical and physical stability at various pHs. Table 4 summarizes the clindamycin potency over time at various pHs when stored at 40° C. As shown in Table 4, initial concentrations of clindamycin in samples 1, 3, and 4 were 9.75, 8.54, and 8.81. After three months storage at 40° C., the concentrations clindamycin in each of these three samples were 9.19, 7.83, and 7.88, respectively. In each case, more than 89% of the concentration of clindamycin remained after 3 months of storage at 40° C.

TABLE 4

| Sample No. | pH | Initial | 1 Mo. | 2 Mo. | 3 Mo. |
|---|---|---|---|---|---|
| 1 | 4.95 | 9.75 | 9.91 | — | 9.19 |
| 2 | 5.93 | 11.29 | 11.40 | 11.12 | — |
| 3 | 6.01 | 8.54 | — | — | 7.83 |
| 4 | 6.29 | 8.81 | — | — | 7.88 |

Table 5 summarizes the physical stability of the clindamycin solution over time at various pHs when stored at room temperature.

TABLE 5

| Sample No. | pH | Initial | 1 Mo. | 2 Mo. | 3 Mo. |
|---|---|---|---|---|---|
| 1 | 4.95 | clear soln | Heavy ppt. | Heavy ppt. | Heavy ppt. |
| 2 | 5.69 | clear soln | ppt. | ppt. | ppt. |
| 3 | 5.93 | clear soln | clear | clear | clear |
| 4 | 6.01 | clear soln | clear | clear | clear |
| 5 | 6.20 | clear soln | clear | clear | clear |
| 6 | 6.29 | clear soln | clear | clear | clear |

Example 15

The stability of benzoyl peroxide suspension was studied for chemical and physical stability at various pH conditions at 40° C. Table 6 shows the physical stability as well as the assay results for benzoyl peroxide. As shown in Table 6, the initial concentration of benzoyl peroxide in the composition having a pH of 6.23 was 6.36%, that of the composition having a pH of 5.80 was 8.19%, and that of the composition having a pH of 4.31 was 6.04%. After 3 months storage at 40° C., the concentration of benzoyl peroxide was 6.06%, or 97% of the initial concentration, 8.16, or 99% of the initial concentration, and 5.89%, or 97% of the initial concentration, respectively. In each case, more than 95% benzoyl peroxide was retained after 3 months.

TABLE 6

| pH | Test | Initial | 1 Mo. | 2 Mo. | 3 Mo. |
|---|---|---|---|---|---|
| 6.23 | Benzoyl Peroxide Assay (%) | 6.36 | — | 6.42 | 6.06 |
|  | Physical Stability | Homogeneous white gel | No change | No change | No change |
| 5.80 | Benzoyl Peroxide Assay (%) | 8.19 | 8.19 | 8.39 | 8.16 |
|  | Physical Stability | Homogeneous white gel | No change | No change | No change |
| 4.31 | Benzoyl Peroxide Assay (%) | 6.04 | 6.22 | 6.02 | 5.89 |

TABLE 6-continued

| pH | Test | Initial | 1 Mo. | 2 Mo. | 3 Mo. |
|---|---|---|---|---|---|
| 4.22 | Physical Stability | Homogeneous white gel | No change | No change | No change |
| | Benzoyl Peroxide Assay (%) | 5.91 | 5.96 | — | — |
| | Physical Stability | Homogeneous white gel | No change | No change | No change |

Example 16

Figure 2:
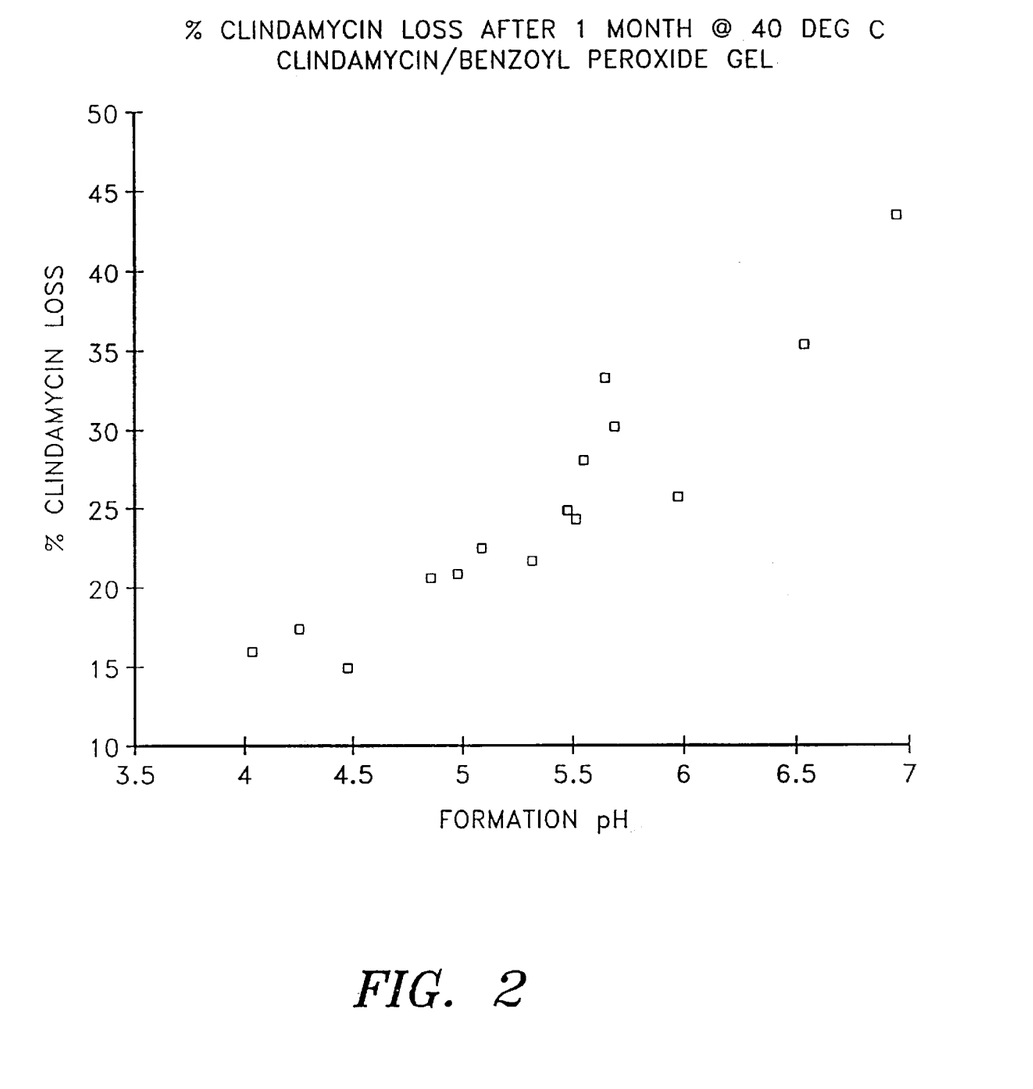
FIG. 2 illustrates the loss of clindamycin in an experimental formulation according to the present invention after admixture of the components and accelerated aging for one month at 40° C.

The chemical stability of the composition containing both clindamycin and benzoyl peroxide, as the kit components are admixed by a pharmacist at the time of dispensing, was studied in an accelerating aging protocol (40° C.). The effect of pH on stability of clindamycin in the presence of benzoyl peroxide is shown in Table 7 and FIG. 2. As shown in Table 7, when the pH of the composition is below about 5.5, about 25% or less of the clindamycin is lost after storage for one month at 40° C.

TABLE 7

| Sample | pH | Loss after 1 month of aging at 40° C. |
|---|---|---|
| 1 | 6.96 | 43.3 |
| 2 | 6.55 | 35.3 |
| 3 | 5.99 | 25.5 |
| 4 | 5.71 | 30.0% |
| 5 | 5.66 | 33.3% |
| 6 | 5.57 | 27.9% |
| 7 | 5.54 | 24.0% |
| 8 | 5.49 | 24.7% |
| 9 | 5.32 | 21.6% |
| 10 | 5.08 | 22.3% |
| 11 | 4.97 | 20.7% |
| 12 | 4.85 | 20.5% |
| 13 | 4.47 | 14.9 |
| 14 | 4.25 | 17.3 |
| 15 | 4.03 | 15.9 |

Example 17

Both clindamycin and benzoyl peroxide in the admixed gel from Example 10 were found to have a shelf-life of several months at room temperature, as illustrated in Table 8. As shown in Table 8, the original concentrations of clindamycin and benzoyl peroxide were 1.20% and 5.87%, respectively. After 2 months the concentration of clindamycin was 1.08% and of benzoyl peroxide was 5.83%. Thus, after two months storage at room temperature, 90% of the original concentration of clindamycin and 99% of the original concentration of benzoyl peroxide remained in the admixed gel.

TABLE 8

| | Initial | 1 Mo. | 2 Mo. | 3 Mo. |
|---|---|---|---|---|
| Clindamycin | 1.20% | — | 1.08% | 1.01% |
| Benzoyl Peroxide | 5.87% | — | 5.83% | 5.97% |
| Physical Appearance | Pleasant smelling, homogeneous white gel | No Change | No change | No change |

Example 18

Five patients with moderate acne vulgaris were treated with the topical gel of Example 10 for six weeks. Each patient applied the gel to his or her face twice daily. Results were evaluated by a dermatologist at weeks 2, 4, and 6, following a baseline pre-treatment evaluation.

In each patient, there was a marked reduction in the number of acne lesions during therapy as set forth in Table 9.

TABLE 9

| Age (years) | 20 | 16 | 17 | 18 | 22 |
|---|---|---|---|---|---|
| Gender | female | female | male | female | female |
| Number of Inflammatory Lesions Before Treatment | 29 | 14 | 14 | 12 | 14 |
| After Treatment | 6 | 8 | 7 | 7 | 0 |
| Number of Non-Inflammatory Lesions Before Treatment | 26 | 126 | 28 | 41 | 8 |
| After Treatment | 12 | 102 | 14 | 36 | 3 |
| Dermatologist Assessment | E | G | VG | G | E |

E = Excellent
VG = Very Good
G = Good

The dermatologist concluded that the topical gel was highly efficacious in reducing the number of inflammatory and non-inflammatory acne lesions. The dermatologist further concluded that the cosmetic elegance of the topical gel of the present invention (compared to the acne preparations previously used by the patients) likely contributed to the apparent high level of patient compliance in following the twice-a-day protocol regimen, thus contributing to the observed high efficacy. Each of the five patients rated the cosmetic elegance of the topical gel of the present invention as being "excellent" or "good," and every one rated its cosmetic elegance "better" than that of his or her previous or usual topical acne therapy.

Example 19

The material from Example 10 was compared to commercially available Benzamycin® (the commercial product corresponding to U.S. Pat. No 4,497,794), each product having been admixed according to directions. Pharmaceutical appearance and physical properties were assessed. The composition of the present invention was found to be superior to Benzamycin® in pharmaceutical elegance, as shown below in Table 10.

TABLE 10

| Quality | Topical Gel of Example 10 | Benzamycin ® Lot # 89449 |
|---|---|---|
| Appearance | Soft, shiny white gel | Dull, rubbery white gel |
| Homogeneity | Uniform | Grainy/syneresis |

Example 20

An experiment was performed to determine the time required by the dispensing pharmacist to compound (admix) the kit in Example 10. For comparison, the same individual compounded Benzamycin® according to the manufacturer's instructions. The invention of the present application provided a significant saving of time for the pharmacist. The results are set forth in Table 11.

TABLE 11

| | Kit of Example 10 | Benzamycin ® Lot # 89449 |
|---|---|---|
| Time to prepare liquid component | 0 sec | 1 min, 15 sec |
| Time to mix components completely (visual end point) | 32 sec | 1 min, 20 sec |
| Total time for pharmacist compounding | 32 sec | 2 min, 25 sec |

Example 21

Thirteen human volunteers participate in a single-blind simultaneous bilateral symmetrical paired comparison of the topical gel of Example 10 and Benzamycin®. The gel from Example 10 was applied to one side of the face in a conventional manner. Benzamycin® was applied to the other side of the face in the same manner. A questionnaire was given to the patients to assess the results. The topical gel of the present invention was highly preferred in each of the properties set forth in Table 12, and therefore represents a distinct improvement over Benzamycin®. Comments made by the volunteers further demonstrate the advantages and improvements. See Table 13.

TABLE 12

| | Composition Preferred (No. of subjects) | | |
|---|---|---|---|
| Cosmetic Property | Topical Gel of Example 10 | Benzamycin Lot # 89449 | No Preference |
| Spreadability | 13 | 0 | 0 |
| Feel/texture during application | 13 | 0 | 0 |
| Rub-in properties | 13 | 0 | 0 |
| Odor | 8 | 4 | 1 |
| Skin feel after application | 10 | 1 | 2 |
| Overall preference | 13 | 0 | 0 |

TABLE 13

Descriptive evaluation of cosmetic properties:

| | Typical volunteer comments |
|---|---|
| Benzamycin Lot # 89449 | cold, chunky, difficult to spread, sticky, tendency to "ball-up," left residue, and dries slowly. |
| Example 10 | aesthetically pleasant to use, easily spread, rubs in quickly, dries quickly, and is totally absorbed by skin. |

Example 22

The stability at room temperature (about 23° C.), at 27° C., and at 40° C. of the clindamycin/benzoyl peroxide composition of the invention as prepared according to Example 10 was compared with that of Benzamycin®, prepared according to instructions on the package insert as in Example 19. This test compared the composition of the invention containing clindamycin and benzoyl peroxide concentrations within the preferred range to the closest composition of the prior art in its commercial form, the components of which are within the preferred range as disclosed in U.S. Pat. No. 4,497,794 (Klein et al.).

Containers of each product were stored under each of the three temperature conditions. Samples of each product were analyzed, using methods of the U.S. Pharmacopeia, at various times to determine the percentage of the antibiotic retained in the composition at the end of each time period. Samples of each product were tested at the initial time before storage. One sample of each product was tested after storage of two weeks and at 1 month for all three storage conditions. Samples were additionally tested at 6 weeks for room temperature, at 8 days and at 6 weeks for 27° C., and at 6 days for 40° C. The results are shown in Table 14.

TABLE 14

| | Percent Antibiotic Remaining After Storage | | | | | | | | | |
|---|---|---|---|---|---|---|---|---|---|---|
| | Room Temperature | | | 27° C. | | | | 40° C. | | |
| | 2 Weeks | 1 Month | 6 Weeks | 8 Days | 2 Weeks | 1 Month | 6 Weeks | 6 Days | 2 Weeks | 1 Month |
| Clindamycin/ Benzoyl Peroxide | 98.6 | 99.1 | 98.1 | 98.5 | 98.3 | 98.2 | 98.1 | 96.0 | 91.7 | 82.6 |
| Benzamycin | 91.0 | 58.3 | 19.4 | 93.4 | 60.3 | <33.8 | <16.6 | <18.6 | <33.8 | <16.6 |

As shown in Table 14, the clindamycin/benzoyl peroxide composition of the invention had greater stability at all three storage conditions. Greater than 98% of the antibiotic remained in the clindamycin/benzoyl peroxide composition after 6 weeks of storage at room temperature and at 27° C. This contrasts to Benzamycin, for which only 19% and 17% of the antibiotic remained after 6 weeks of storage at room temperature and at 27° C., respectively. Additionally, after 2 weeks of storage at 40° C., almost 92% of the antibiotic remained for clindamycin/benzoyl peroxide whereas only about one third of the antibiotic remained in Benzamycin.

No change in physical appearance was observable in the clindamycin/benzoyl peroxide composition throughout the 6 week room temperature storage period, and only slight syneresis was noted throughout the 6 week storage period at 27° C. and the one month storage period at 40° C. In contrast, after 1 month storage at room temperature, Benzamycin developed light yellow spots and, after 6 weeks, the product was grainy and clumpy, with yellow specks. At 27° C., Benzamycin developed light yellow spots after one month and, at 6 weeks, was grainy and clumpy with yellow specks. At 40° C., Benzamycin developed separation, yellow spots, and an offensive odor after one month storage.

Example 23

In a double blind study, the clinical anti-acne effectiveness of the composition of the invention containing 1% clindamycin phosphate and 5% benzoyl peroxide was compared to that of a composition containing the same vehicle as for the composition of the invention but with 1% clindamycin phosphate without benzoyl peroxide and of a composition containing the same vehicle as for the composition of the invention but with 5% benzoyl peroxide without clindamycin.

Ninety patients with mild to moderate facial acne vulgaris were randomly assigned to one of three drug treatment groups, with 30 patients assigned to each of the clindamycin/benzoyl peroxide (CLN/BEN) group, the clindamycin (CLN) group, and the benzoyl peroxide (BEN) group. Each patient in the study had between 12 and 70 inflammatory facial lesions and between 10 and 30 non-inflammatory facial lesions.

Patients in each treatment group applied in the morning and at night a pea-sized globule of the blinded composition on their forehead and on each cheek and smoothed the medication over their face, from hairline to jawline, excluding the nose. Unused medication was stored at room temperature.

The patients were examined initially before treatment, and at the end of 1, 2, 4, 6, 8, and 10 weeks. The primary efficacy parameter measured was the reduction in the number of inflammatory lesions. Secondary efficacy parameters included the reduction in the number of non-inflammatory lesions and a physician's global assessment.

A. Inflammatory Lesions:

As shown in Table 15, there was a greater reduction in the number of inflammatory lesions in the CLN/BEN group compared to the other two groups as early as the first evaluation at Week 1. This superiority was maintained throughout the entire study. At Week 10, the group treated with CLN/BEN had a statistically significantly greater percent reduction in inflammatory lesions compared to the group treated with CLN ($p<0.5$).

TABLE 15

Mean Percent Reduction from Baseline in Inflammatory Lesions

| Treatment | 1 Week (%) | 2 Week (%) | 4 Week (%) | 6 Week (%) | 8 Week (%) | 10 Week (%) |
|---|---|---|---|---|---|---|
| CLN/BEN | 53 | 58 | 71 | 76 | 74 | 80 |
| CLN | 33 | 47 | 59 | 54 | 61 | 65 |
| BEN | 40 | 58 | 62 | 66 | 59 | 69 |

B. Non-Inflammatory Lesions:

As shown in Table 16, there was also a pattern of greater efficacy for CLN/BEN versus CLN or BEN in treating non-inflammatory lesions throughout the entire study.

TABLE 16

Mean Percent Reduction from Baseline in Non-Inflammatory Lesions

| Treatment | 1 Week (%) | 2 Week (%) | 4 Week (%) | 6 Week (%) | 8 Week (%) | 10 Week (%) |
|---|---|---|---|---|---|---|
| CLN/BEN | 40 | 50 | 55 | 55 | 62 | 70 |
| CLN | 20 | 34 | 38 | 48 | 52 | 64 |
| BEN | 42 | 53 | 55 | 59 | 59 | 62 |

C. Physician's Global Assessment:

A global assessment by the investigator (physician) of each patient's acne vulgaris was made at each visit following the initial evaluation. This assessment served as an overall measure of response to treatment. Each patient was rated by the investigator at each visit as Cleared, Excellent, Good, Fair, Poor, Unchanged or Worse.

As shown in Table 17, after the first week of treatment, patients in the CLN/BEN group were consistently rated better than patients in either of the CLN or BEN groups. The superiority of the CLN/BEN treatment was especially marked at Week 10, when 61% of CLN/BEN patients were rated as either Cleared or Excellent versus only 29% of CLN and 48% of BEN patients respectively.

TABLE 17

Physician's Global Assessment
Percent of Patients Rated Cleared or Excellent

| Treatment | 1 Week (%) | 2 Week (%) | 4 Week (%) | 6 Week (%) | 8 Week (%) | 10 Week (%) |
|---|---|---|---|---|---|---|
| CLN/BEN | 10 | 10 | 30 | 36 | 46 | 61 |
| CLN | 0 | 7 | 10 | 17 | 31 | 29 |
| BEN | 13 | 10 | 13 | 33 | 37 | 48 |

The results of the clinical study of Example 23 demonstrate that the composition of the invention, comprising clindamycin and benzoyl peroxide, is more efficacious in treating both the inflammatory and non-inflammatory lesions of acne than is a composition containing only clindamycin or benzoyl peroxide. Moreover, the efficacy and superiority of the composition of the invention surprisingly occurred as early as the first week of treatment, its superiority was maintained over the full ten weeks of the study, and by Week 10, it was statistically significantly ($p<0.5$)

more efficacious than clindamycin alone in the primary efficacy variable, the number of inflammatory acne lesions. The great therapeutic difference seen at the end of the ten week treatment period was most surprising, because the respective efficacy of drugs presently used to treat acne tends to converge over time as they are given longer to work.

Example 24

A kit, having a room temperature shelf life of at least 18 months, was prepared which included (a) 6.0 g of the clindamycin aqueous solution concentrate as follows in a 6 mL amber glass screw cap vial:

| Clindamycin Phosphate Solution Concentrate | Percent by Weight |
|---|---|
| Clindamycin (As Clindamycin Phosphate, USP) | 6.00 |
| Methylparaben, NF | 0.20 |
| Propylparaben, NF | 0.03 |
| Potassium Hydroxide, NF | QSAD pH 6.25 |
| Purified Water, USP | QSAD 100.00 |

(b) 24.0 g of the benzoyl peroxide aqueous gel as follows in a one and one-half ounce wide-mouth plastic jar.

| Benzoyl Peroxide Gel | Percent by Weight |
|---|---|
| Benzoyl Peroxide (as Hydrous Benzoyl Peroxide, USP) | 6.56 |
| Propylene Glycol, USP | 12.50 |
| Methylparaben, NF | 0.086 |
| Propylparaben, NF | 0.02 |
| Carbomer 980, NF (Carbopol ®, carboxy vinyl polymer) | 2.19 |
| Potassium Hydroxide, NF | QSAD pH 5.4 |
| Purified Water, USP | QSAD 100.00 | and (c) a disposable mixing spatula.

The components were admixed as follows:

1. The entire contents of the vial of clindamycin solution was added to the jar containing the benzoyl peroxide gel; and
2. Using the disposable plastic spatula, the combination was mixed for about one minute until the gel became homogeneous.

About 30 grams of an aesthetically pleasing, viscous white gel was produced containing about 5.25% benzoyl peroxide and about 1.2% clindamycin, with a pH of between 5.5 and 4.5 during the shelf life. The resultant gel was chemically and physically stable with a shelf life of at least 1 month and at least 4 months at room temperature. The clindamycin and benzoyl peroxide gel prepared from this kit is an effective acne treatment, and particularly more effective than either drug used alone.

Although the foregoing invention has been described in some detail by way of illustration and example for purposes of clarity of understanding, it will be obvious that certain changes and modifications may be practiced within the scope of the appended claims.

What is claimed:

1. A topical therapeutic composition, which has a pH from about 4.0 to less than 7.0 and is stable at room temperature which composition comprises a suspension of benzoyl peroxide and a solution of a pharmaceutical grade of a clindamycin selected from the group consisting of clindamycin phosphate and clindamycin hydrochloride, and the solution of clindamycin, before combination with the benzoyl peroxide, having an adjusted pH in the range from about 5.9 to 6.9.

2. The topical composition of claim 1 which comprises a gelling agent.

3. The topical composition of claim 2 which is a gel composition.

4. The topical composition of claim 3 wherein the gelling agent is a carboxylated polymer.

5. The topical composition of claim 4 wherein the carboxylated polymer is a carboxy vinyl polymer.

6. The composition of claim 5 wherein the carboxy vinyl polymer is carboxypolymethylene.

7. The topical composition of claim of 3 wherein the clindamycin is clindamycin phosphate.

8. The composition of claim 2 which is free of dioctyl sodium sulfosuccinate (DSS).

9. The composition of claim 3 wherein the benzoyl peroxide is an aqueous slurry of benzoyl peroxide powder.

10. The composition of claim 9 wherein the benzoyl peroxide is present in an amount in the range from 1 to 20% by weight.

11. The composition of claim 2 wherein the clindamycin concentration is from 2 to 15% by weight.

12. A topical therapeutic composition, which has a pH from about 4.0 to less than 7.0 and is stable at room temperature, which composition comprises a suspension of benzoyl peroxide and a solution of a pharmaceutical grade of a clindamycin selected from the group consisting of clindamycin phosphate and clindamycin hydrochloride, and the solution of clindamycin, before combination with the benzoyl peroxide, having an adjusted pH in the range from 5.9 to 6.9.

13. The topical therapeutic composition of claim 12 which is free of dioctyl sodium sulfosuccinate (DSS).

14. A topical therapeutic composition, which has a pH from about 4.0 to less than 7.0 and is stable at room temperature, which composition is made by combining a suspension of benzoyl peroxide and a solution of a pharmaceutical grade of a clindamycin selected from the group consisting of clindamycin phosphate and clindamycin hydrochloride, and the solution of clindamycin, before combination with the benzoyl peroxide, having an adjusted pH in the range from 5.9 to 6.9.

15. The topical therapeutic composition of claim 14 which is bee of dioctyl sodium sulfosuccinate (DSS).

* * * * *

UNITED STATES PATENT AND TRADEMARK OFFICE
CERTIFICATE OF CORRECTION

PATENT NO : 6,117,843
DATED : September 12, 2000
INVENTOR(S): Lloyd J. Baroody, Gordon J. Dow, Debra A. Dow, Robert Lathrop It is certified that error appears in the above-identified patent and that said Letters Patent are hereby corrected as shown below:

In claim 15, at column 18, line 59, delete "bee", and replace with --free--.

Signed and Sealed this

Twenty-fourth Day of April, 2001

Attest:

NICHOLAS P. GODICI

Attesting Officer

Acting Director of the United States Patent and Trademark Office